United States Patent [19]

Pradier et al.

[11] Patent Number: 5,679,361
[45] Date of Patent: Oct. 21, 1997

[54] SOLID OR PASTY MAKE-UP COMPOSITION

[75] Inventors: François Pradier, Fontenay-Aux-Roses; Elisabeth Maison-Belhomme, Vincennes; Christian Felardos, Chevilly Larue, all of France

[73] Assignee: L'Oreal, Paris, France

[21] Appl. No.: 551,035

[22] Filed: Oct. 31, 1995

Related U.S. Application Data

[63] Continuation of Ser. No. 256,649, filed as PCT/FR93/01274, Dec. 21, 1993, published as WO94/14402, Jul. 7, 1994, abandoned.

[30] Foreign Application Priority Data

Dec. 24, 1992 [FR] France .................. 92 15728

[51] Int. Cl.⁶ .................................................. A61K 7/00
[52] U.S. Cl. ......................... 424/401; 424/489; 514/844
[58] Field of Search ....................... 424/401, 489–502, 424/63, 64, 65; 514/844

[56] References Cited

U.S. PATENT DOCUMENTS

| | | | |
|---|---|---|---|
| 4,624,577 | 11/1986 | Vannier et al. | 366/83 |
| 4,844,935 | 7/1989 | Fere et al. | 426/549 |
| 5,035,885 | 7/1991 | Arraudeau et al. | 424/78 |
| 5,206,012 | 4/1993 | Farer | 424/69 |
| 5,219,561 | 6/1993 | Gagnebien et al. | 424/69 |
| 5,234,682 | 8/1993 | Macchio | 424/69 |

FOREIGN PATENT DOCUMENTS

| | | |
|---|---|---|
| 0 486 394 | 5/1992 | European Pat. Off. . |
| 1 586 848 | 1/1970 | France . |
| 3-47110 | 2/1991 | Japan . |
| 2 027 341 | 2/1980 | United Kingdom . |

Primary Examiner—Gollamudi S. Kishore
Attorney, Agent, or Firm—Young & Thompson

[57] ABSTRACT

A solid or pasty extruded homogeneous make-up composition containing a fatty phase and a pulverulent phase. The fatty phase is 20–70% by weight of the total weight of the composition. The pulverulent phase is a light powder having a specific gravity not exceeding 0.07, and can be silica powder or hollow microspheres made of thermoplastic material. The light powder is 5–30% by weight of the total weight of the composition. The weight ratio of the total pulverulent phase to the light powder is between 5 and 16.

3 Claims, 1 Drawing Sheet

SOLID OR PASTY MAKE-UP COMPOSITION

This application is a continuation of application Ser. No. 08/256,649, filed as PCT/FR93/01274 Dec. 21, 1993 published as WO94/14402 Jul. 7, 1994, now abandoned.

FIELD OF THE INVENTION

The present invention relates to a make-up composition containing a high proportion of light powder.

BACKGROUND OF THE INVENTION

It is known to prepare solid or pasty make-up compositions of two types containing pulverulent products:

cast compositions, which are prepared by mixing a fatty phase in the molten state with pulverulent products, with or without volatile solvent;

compacted compositions, which are prepared by mixing a pulverulent product with a fatty binder and subjecting the mixture to a compression.

These two types of compositions are conventionally prepared with powders which have a relative density higher than approximately 0.5. It would be desirable to introduce light powders, that is to say ones with a relative density not exceeding 0.07, into these make-up compositions to improve their feel. However, until now, only limited quantities of light powders could be introduced, these quantities generally not exceeding approximately 4.5% by weight of the composition.

In fact, beyond this limited proportion, in the case of compositions cast without volatile solvent, it becomes difficult or even impossible with the usual processes to homogenize the mixture of fatty phase and of pulverulent products and, consequently, the mixture obtained is difficult or even impossible to cast. In the case of compacted compositions the introduction of large quantities of light pulverulent products also entails a difficulty in homogenizing. It was therefore difficult hitherto to obtain homogeneous compositions that could be employed for make-up with a high proportion of light powders.

SUMMARY OF THE INVENTION

According to the present invention it has been found that by employing a single- or twin-screw cooker-extruder mixer for the preparation of solvent-free cast or compacted compositions it is possible to obtain fully homogeneous compositions which can be employed for make-up, containing up to 30% by weight of powder with a relative density not exceeding 0.07.

The subject of the present invention is therefore a solid or pasty make-up composition containing a fatty phase and a pulverulent phase, the pulverulent phase consisting at least partially of a light powder, characterized in that the light powder has a relative density not exceeding 0.07 and represents from 5 to 30% by weight relative to the total weight of the composition, the weight ratio of the total pulverulent phase to the light powder being between 5 and 16 and in that the fatty phase represents from 20 to 70% by weight relative to the total weight of the composition.

According to the invention the fatty phase preferably represents from 20 to 50% by weight of the composition, the pulverulent phase consequently representing from 50 to 80% by weight of the composition, which corresponds to the manufacture of make-up compositions of the cast type or of the compacted type.

The light powder with a relative density not exceeding 0.07 may comprise at least one of the following constituents:

hollow microspheres made of thermoplastic material and prepared by known processes such as those described in U.S. Pat. No. 3,615,972 and EP-A-056,219. These microspheres can be made of any nontoxic and nonirritant thermoplastics, for example of polymers or copolymers of ethylene derivatives such as polyethylene, polystyrene, vinyl chloride-acrylonitrile copolymer or polyacrylonitrile, of polyamides, of polyesters, of urea-formaldehyde polymers or of vinylidene chloride copolymers (such as vinylidene chloride-acrylonitrile). It is possible to mention especially the microspheres marketed under the trade name "Expancel" by the company "Kemanord Plast" or under the trade name "Micropearl F 80 ED" by the company "Matsumoto";

silica powder, for example that marketed under the trade name "Cab-O-Sil TS-530" by the "Cabot" company.

The pulverulent phase advantageously contains powders which have a density that is higher than that of the light powder. These powders may be any known powder usually employed for the preparation of make-up compositions, it being possible for these powders to comprise at least one pigment and/or at least one filler.

The pigments may be chosen from inorganic pigments, organic pigments and pearly pigments.

Among inorganic pigments there may be mentioned by way of examples:

titanium dioxide (rutile or anatase), optionally surface-treated and codified in the "Colour Index" (CI) under reference CI 77891;

black, yellow, red and brown iron oxides (CI 77499, 77492, 77491);

manganese violet (CI 77742);

ultramarine blue (CI 77007);

chromium oxide (CI 77288);

chromium oxide hydrate (CI 77289); and ferric blue (CI 77510).

Among organic pigments there may be mentioned, for example, the pigments: D & C Red No. 19 (CI 45170), D & C Red No. 9 (CI 15585), D & C Red No. 21 (CI 45380), D & C Orange No. 4 (CI 15510), D & C Orange No. 5 (CI 45370), D & C Red No. 27 (CI 45410), D & C Red No. 13 (CI 15630), D & C Red No. 7 (CI 15850:1), D & C Red No. 6 (CI 15850:2), D & C Yellow No. 5 (CI 19140), D & C Red No. 36 (CI 12085), D & C Orange No. 10 (CI 45425), D & C yellow No. 6 (CI 15985), D & C Red No. 30 (CI 73360), D & C Red No. 3 (CI 45430), carbon black (CI 77266) and lakes based on cochineal carmine (CI 75470).

Pearly pigments may be chosen especially from:

white pearly pigments, such as mica covered with titanium oxide or bismuth oxychloride; and coloured pearly pigments such as titanium mica with iron oxides, titanium mica with ferric blue or chromium oxide, titanium mica with an organic pigment of the abovementioned type and pigments based on bismuth oxychloride.

These pigments may represent up to 30% by weight relative to the total weight of the composition.

The fillers are chosen especially from:

talc, which is a hydrated magnesium silicate employed in the form of particles generally smaller than 40 µm in size; talc has moisture-absorbing properties and is employed above all because of its smooth feel;

micas, which are aluminosilicates of various compositions, which are in the form of flakes from 2 to 200 µm in size, preferably from 5 to 70 µm and with a thickness of 0.1 to 5 µm, preferably from 0.2 to 3 µm; micas may be of natural origin (for example muscovite, margarite, roscoelite, lipidolite, biotite) or of synthetic origin; micas are generally transparent and make it possible to give a satin appearance to the skin;

starch, in particular rice starch;

kaolin, which is a hydrated aluminium silicate, which is in the form of particles of isotropic forms generally smaller than 30 µm in size and which has good absorption properties for fatty substances;

zinc and titanium oxides, generally employed in the form of particles whose size does not exceed a few micrometers (or even smaller than 1 µm in the case of titanium oxide); these oxides have a smooth feel, have a good covering power and have a high opacity;

precipitated calcium carbonate which, in the form of particles smaller than 10 µm in size, has a smooth feel and allows a matt appearance to be obtained;

magnesium carbonate and hydrocarbonate, which have especially perfume-binding properties;

silica;

titanium dioxide;

metallic soaps derived from carboxylic organic acid containing from 8 to 22 carbon atoms, preferably from 12 to 18 carbon atoms, for example zinc, magnesium or lithium stearate, zinc laurate, magnesium myristate; these soaps, which are generally present in the form of particles smaller than 10 µm in size, have a smooth feel and make it easier for the powder to adhere to the skin;

unexpanded synthetic polymer powders, such as polyethylene, polyesters (for example polyethylene isophthalate or terephthalate) and polyamides (for example nylon), in the form of particles smaller than 50 µm in size, which have absorbent properties and make it possible to impart a velvety appearance to the skin.

Those more particularly employed are inorganic powders such as spherical silica, spherical titanium dioxides such as "Spherititan" (registered mark), glass and ceramic beads marketed by the "3M" company under the trade names "Macrolites"; powdered organic materials of natural origin, such as corn, wheat or rice starches, crosslinked or otherwise; spheronized synthetic polymer powders (optionally crosslinked) such as powdered polyamides (for example nylon or poly-β-alanine), polyethylene, polymethacrylic acids, polystyrene (crosslinked with divinylbenzene), silicone resin, Teflon (for example: "Fluon" particles marketed by the "Montefluos" company and "Hostaflonq" particles marketed by the "Hoechst" company).

These fillers may represent up to 80% by weight relative to the total weight of the composition.

Pigments and fillers may be coated with substances such as amino acids, silicones, metal salts or collagen, specially in order to modify their surface quality.

The fatty phase consists of at least one fatty binder which is liquid or solid at ambient temperature and/or at least one oil-soluble synthetic polymer the use of which in cosmetics is known.

Among the binders there may be mentioned, in particular, fatty oils or substances of animal, vegetable, mineral or synthetic origin, waxes or their mixtures.

The fatty oils or substances are, in particular, chosen from mink oil, turtle oil, soya oil, grape seed oil, sesame oil, corn oil, rapeseed oil, sunflower oil, cotton oil, avocado oil, olive oil, castor oil, jojoba oil or groundnut oil, a hydrocarbon oil such as liquid paraffin, squalane or Vaseline, esters such as isopropyl myristate, isopropyl palmitate, butyl stearate, hexyl laurate, isononyl isononanoate, 2-ethylhexyl palmitate, 2-hexyldecyl laurate, 2-octyldecyl palmitate, 2-octyldodecyl myristate, di-2-ethylhexyl succinate, diisostearyl malate, 2-octyldodecyl lactate, glycerine triisostearate or diglycerine triisostearate, a silicone oil such as polymethylsiloxanes, polymethylphenylsiloxanes, polysiloxanes modified with fatty acids, polysiloxanes modified with fatty alcohols, polysiloxanes modified with polyoxyalkylenes, fluorinated silicones, perfluorinated and/or organofluorinated oils, higher fatty acids such as myristic acid, palmitic acid, stearic acid, behenic acid, oleic acid, linoleic acid, linolenic acid or isostearic acid, and higher fatty alcohols such as cetanol, stearyl alcohol or oleyl alcohol.

The waxes may be chosen from the group made up of animal waxes, vegetable waxes, mineral waxes, synthetic waxes and various fractions of natural waxes. Among the animal waxes which can be employed there may be mentioned beeswax, lanolin waxes and Chinese insect waxes. Among vegetable waxes there may be mentioned carnauba, candelilla and ouricury wax, cork fibre waxes, sugar cane waxes, Japan waxes, hydrogenated jojoba waxes and hydrogenated oils which are obtained by catalytic hydrogenation of fatty substances composed of a $C_8$–$C_{32}$ linear or nonlinear fatty chain and which have properties corresponding to the definition of waxes. There may be mentioned, in particular, hydrogenated sunflower oil, hydrogenated castor oil, hydrogenated copra oil and hydrogenated lanolin. Among the mineral waxes there may be mentioned paraffin waxes, microcrystalline waxes, montan waxes and ozokerites. Among the synthetic waxes there may be mentioned polyethylene waxes, the waxes obtained by the Fischer and Tropsch synthesis, waxy copolymers and their esters and silicone waxes such as polyalkoxy- and polyalkylsiloxanes.

The fatty phase may, in a known manner, contain at least one lipophilic cosmetic agent.

Various other ingredients may be introduced into the compositions according to the invention, such as astringent agents, which are employed in deodorizing powders or in foot powders, such as aluminium hydroxychloride or alums, sunscreens, softening agents, moisturizing agents (for example sorbitol or glycerine), cicatrizing agents, agents against free radicals, vitamins or perfumes.

These ingredients may represent up to 5% by weight relative to the total weight of the composition.

Another subject of the present invention is a process for the preparation of the composition described above.

A process for the preparation of a homogeneous composition consisting of a fatty phase and of a pulverulent phase containing from 5 to 30% by weight of light powder which has a relative density not exceeding 0.07, is characterized in that the mixing is performed in a cooker-extruder mixer comprising one or two screws.

The cooker-extruder mixers which can be employed are pieces of equipment of known type, commonly used especially in the food industry and the chemical industry. These mixers comprise an outer enclosure fitted with an extrusion die at the exit, inside which enclosure one or two shafts are driven in rotation so that the peripheral structure of one shaft interacts with the outer enclosure and, if appropriate, with the peripheral structure of the other shaft, to ensure mixing of the material and its movement in the outer enclosure towards the extrusion die. The shaft (or each of the shafts) preferably consists of at least two successive sleeves whose inner part is fitted onto an axle driven in rotation and whose outer part may have various peripheral structures; among the conventional structures there may be mentioned, on the one hand, a helical screw flight whose pitch conducts the processed material from the entry towards the exit of the mixer (denoted later as "DF"); on the other hand, a helical screw flight of pitch which is the reverse of the preceding one (denoted later by "CF") which pushes back the processed material in the direction from the exit towards the entry of the mixer, such a flight comprising lengthwise grooves to ensure the travel of the material towards the exit of the mixer; and, finally, a multilobed section comprising over its whole length small blades (or lobes) arranged side by side and offset angularly relative to one another. A bilobed section therefore comprises a succession of lobes offset by 90° relative to one another and is denoted hereinafter as "BL". A fairly large number of sleeves with external flights may be used in order to vary the pitch, the depth and the number of flights in the different successive lengthwise zones of the mixer. In addition, some lengthwise zones of the mixture may be heated by one or more jackets around outside the outer enclosure. The heating may be produced in each jacket with the aid of at least one electrical element or at least one heat exchanger.

The shaft or each shaft of the cooker-extruder mixer preferably comprises at least one "DF" sleeve forming a conveyor screw situated on the feed (or entry) side of the mixer, at least one "CF" (called "counterflight") sleeve and/or a multilobed "BL" sleeve forming a pressurized blending zone, and at least one "DF" sleeve forming a conveyor screw situated at the exit end of the mixer. The apparatus may also comprise at least one sleeve which has a grinding and/or homogenizing action, such as a "BL" bilobed sleeve.

In addition to as a result of the fact that it makes it possible to produce homogeneous make-up compositions containing a high proportion of light powder, the use of a cooker-extruder mixer offers many other advantages. The manufacture can take place continuously and at lower temperature. For example, a "blusher" is conventionally manufactured at a temperature of between 70° and 90° C.; with a cooker-extruder mixer it can be manufactured at 50° C. or less. The fact of operating at a lower temperature makes it possible to avoid degrading the raw materials, for example the expanded powders, and allows heat-sensitive cosmetic agents to he introduced into the make-up composition.

Furthermore, the process according to the present invention is flexible, because the products introduced as feed and the feed rates and, consequently, the formulations can be easily varied. It is also easily possible to vary, as a function of the desired make-up composition, the physical process parameters such as the pressure, especially by affecting the exit section and the speed of rotation of the shafts, the shearing during the treatment, especially through the choice of the multilobed sleeves and of the flight shapes, the blending, especially through the choice of the sleeves of "CF" type, and the temperature, by regulating the heating jackets opposite the different zones of the mixer.

The examples given below, by way of illustration and without any limitation being implied, will allow the invention to be better understood.

EXAMPLE 1

Preparation of a "Blusher"

A) Extruder mixer employed

The operation is carried out in a twin-screw cooker-extruder mixer (type "BC 21" from the "Clextral" company), the structure of which is that shown diagrammatically below:

| Entry → | | | | | | | | | | | | → Exit |
|---|---|---|---|---|---|---|---|---|---|---|---|---|
| Screw structure | DF | DF | DF | DF | BL | DF | DF | CF | DF | DF | BL | DF |
| Length of the sleeves (mm) | 50 | 50 | 50 | 50 | 50 | 100 | 50 | 25 | 50 | 50 | 50 | 25 |
| Screw pitch length (mm) | 16.6 | 16.6 | 16.6 | 16.6 | | | 25 | 16.6 | 16.6 | 16.6 | 16.6 | 16.6 |

DETAILED DESCRIPTION OF THE INVENTION

Figure 1:
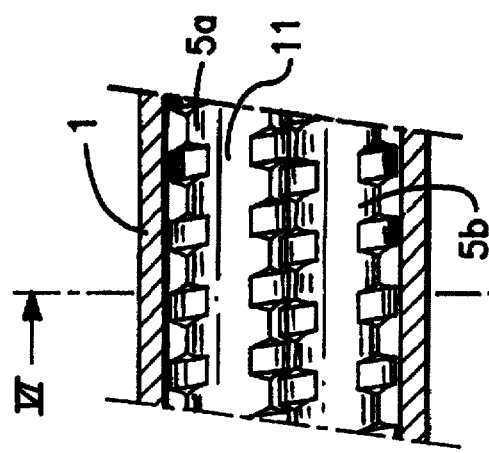
FIGS. 1, 3 and 5 represent, in elevation, sections of different types of sleeves employed on the shafts of the mixer used in Example 1.

With reference to the drawing, it can be seen that 1 has been used to denote the outer enclosure of the mixer and 2a, 2b the axles of the two parallel shafts which are placed therein. Adjacent sleeves are slipped onto the axles 2a, 2b, the two shafts being fitted with the same sleeves on the same single section of the length in order to interact mechanically with each other during the rotation.

Figure 2:
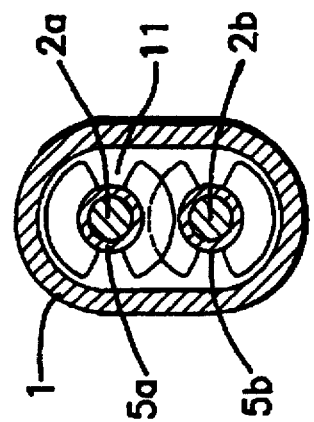
FIGS. 2, 4 and 6 show, respectively, cross-sections along II—II, IV—IV and VI—VI of FIGS. 1, 3 and 5.
Figure 3:
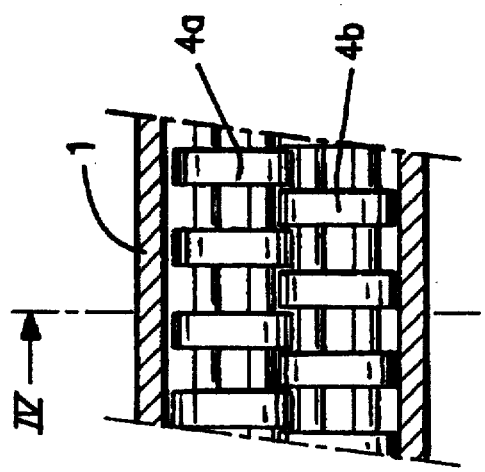
Figure 4:
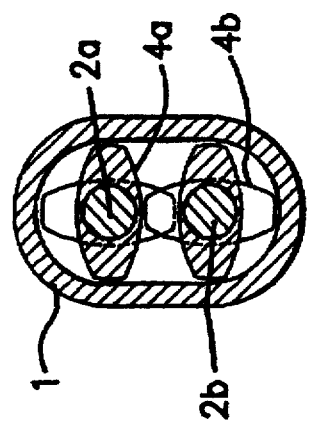
Figure 5:
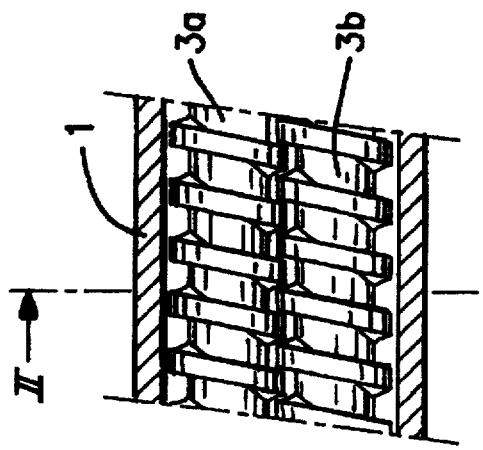
Figure 6:
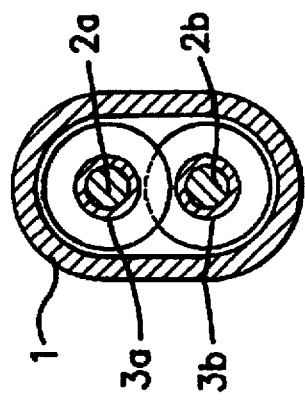

In FIGS. 1 and 2, a section has been shown where sleeves of "DF" type, referred to as 3a, 3b, are situated. In FIGS. 3 and 4 a section has been shown where sleeves 4a, 4b of "BL" bilobed type are situated. In FIGS. 5 and 6 a section has been shown where sleeves 5a, 5b of "CF" type with lengthwise grooves 11 are situated.

In the table given below:

DF denotes a screw member with twin helical flight, as illustrated in FIGS. 1 and 2;

BL denotes a bilobed member, as illustrated in FIGS. 3 and 4; and

CF denotes a screw member with a pitch which is the reverse of DF, as illustrated in FIGS. 5 and 6, comprising lengthwise grooves 11.

The various members have an outer diameter of 25 mm and an inner diameter of 14 mm; the distance between the axles of the two shafts is 21 mm. The two shafts rotate at the rate of 300 rev/min; the exit orifices have a total section of 500 mm$^2$; the throughput is approximately 5 kg/h. The mixer is heated to 50° C. over its whole length.

B) Formulation

The formulation is the following (weights given in g):

| Fatty phase: | |
|---|---|
| Polyethylene wax | 4 |
| Microcrystalline wax | 1 |
| Vaseline | 7 |
| Isostearyl neopentanoate | 8.5 |
| Liquid paraffin | 15 |
| Octyldodecanol | 10 |

| Pulverulent phase: | |
|---|---|
| Yellow iron oxide | 0.5 |
| Brown/yellow iron oxide | 2.2 |
| Titanium oxide | 5 |
| Lithol B calcium red lake on rosin | 0.3 |
| Nylon powder | 21 |
| Microsphere which has a jacket made of vinylidene/acrylonitrile/methacrylate copolymer and contains isobutane (0.036 relative density "Expancel") | 8.5 |
| Propyl parahydroxybenzoate | 0.2 |
| Perfume | 0.3 |

The pulverulent phase is fed at the head of the screw; the fatty phase is pumped and then fed at 100 mm from the head; the exit orifices have a total section of 314 mm$^2$; the perfume is introduced by means of a peristaltic pump near the end of the screw.

An orangy-red "blusher" is obtained of very homogeneous appearance, very soft to the touch and with a pleasant original texture.

By way of comparison, mixing of the same composition was performed in a "VMI" kneader marketed by the "Kenwood" company, in a "Baker"-type mixer and in a blade stirrer of "Stephan" type. It can be seen with the unaided eye that the mixture obtained is not homogeneous. It was not possible to produce such a mixture with a vessel fitted with a "Broglie" turbine with counter-rotating paddles.

EXAMPLE 2

Preparation of a Foundation

The operation is carried out in the same cooker-extruder mixer as in Example 1, with the following screw structure:

| Entry | | | | | | | | | | → Exit |
|---|---|---|---|---|---|---|---|---|---|---|
| Screw structure | DF | DF | BL | DF | DF | CF | DF | DF | DF | DF |
| Length of the sleeves (mm) | 100 | 100 | 50 | 100 | 50 | 25 | 50 | 50 | 50 | 25 |
| Screw pitch length (mm) | 25 | 25 | | 25 | 16.6 | 16.6 | 16.6 | 16.6 | 16.6 | 16.6 |

(DB, BL and CF have the same meaning as in Example 1).

The members have the same radial dimensions as in Example 1 and the axles have the same separation and the same speed of rotation; the exit orifices have a total section of 48 mm$^2$; the feed rate is also approximately 5 kg/h.

The formulation of the composition is the following (weight given in g):

| Fatty phase | |
|---|---|
| 2-Ethylhexyl palmitate | 12.2 |
| Hydrogenated isoparaffin | 19.7 |
| Stabilized isopropyl lanolate | 5.8 |
| Propyl para-hydroxybenzoate | 0.3 |
| Perfume | 0.3 |
| Microcrystalline wax | 10 |
| Carnauba wax | 6 |

| Pulverulent phase | |
|---|---|
| Yellow iron oxide | 2.1 |
| Brown/yellow iron oxide | 0.8 |
| Black iron oxide | 0.3 |
| Titanium oxide | 12 |
| Nylon 12 powder | 17.2 |
| Magnesium silicate | 7 |
| Microsphere which has a copolymer jacket (vinylidene/acrylonitrile/methacrylate) and contains isobutane (0.036 relative density "Expancel") | 6 |

The fatty phase and the pulverulent phase are introduced at the head of the screw by means of a peristaltic pump and a weight-dispenser.

The foundation obtained is golden brown, very soft to the touch and very homogeneous to the unaided eye.

We claim:

1. A process for the preparation of a homogeneous cosemtic make-up composition containing a fatty phase and a powder, the fatty phase comprising 20–70% by weight of the total weight of the composition; the improvement wherein the powder has a specific gravity not exceeding 0.07, said powder constituting 5–30% by weight of the total weight of the composition, and mixing the composition in a cooker-extruder mixer in an outer enclosure fitted with an extrusion die at the exit and with two shafts driven in rotation so that the peripheral structure of one shaft interacts with the outer enclosure and with the peripheral structure of the outer shaft to ensure mixing of the material and its movement in the outer enclosure toward the extrusion die.

2. A process as claimed in claim 1, wherein the shafts consist of at least two successive sleeves whose inner part is fitted onto an axle driven in rotation and whose outer part has a peripheral structure which differs according to the sleeves.

3. A process as claimed in claim 1, wherein each shaft comprises at least one sleeve forming a conveyor screw situated on the feed side of the mixer, at least one sleeve with at least one of a counterflight and a multi-lobed sleeve, and at least one sleeve forming a conveyor screw situated at the exit end of the mixer.

\* \* \* \* \*